United States Patent [19]

Noguchi et al.

[11] 4,220,040
[45] Sep. 2, 1980

[54] METHOD AND SYSTEM FOR TRANSMISSION AND RECEIPT OF MEASURING ULTRASONIC WAVE

[75] Inventors: Yasuo Noguchi, Yokohama; Taro Kokuzawa, Tokyo; Hideyuki Suzuki, Hamamatsu; Toru Yokose, Zushi, all of Japan

[73] Assignee: Sumitomo Bakelite Company Limited, Tokyo, Japan

[21] Appl. No.: 956,295

[22] Filed: Oct. 31, 1978

[30] Foreign Application Priority Data

Jun. 27, 1978 [JP] Japan .................... 53-76991

[51] Int. Cl.³ .................... G01N 29/02
[52] U.S. Cl. .................... 73/24; 435/807
[58] Field of Search .................... 73/584, 632, 24; 310/317, 319; 435/4, 807

[56] References Cited

U.S. PATENT DOCUMENTS

| | | | |
|---|---|---|---|
| 2,416,337 | 2/1947 | Mason | 310/317 |
| 3,468,157 | 9/1969 | Burk et al. | 73/24 |
| 3,675,472 | 7/1972 | Kay et al. | 73/602 |
| 3,774,717 | 11/1973 | Chodorow | 73/599 |
| 4,119,950 | 10/1978 | Redding | 73/24 |
| 4,156,823 | 5/1979 | Suzuki | 73/584 |

Primary Examiner—Stephen A. Kreitman
Attorney, Agent, or Firm—Karl W. Flocks

[57] ABSTRACT

A measuring ultrasonic wave transmitter comprises a negative immitance converter inserted between an ultrasonic transmitting transducer and a drive amplifier for driving the transmitting transducer. The output impedance of the drive amplifier, the damping impedance of the transmitting transducer and the impedance between the transmitting transducer and the drive amplifier are offset by the negative impedance caused by the negative immitance converter. A measuring ultrasonic wave receiver comprises a negative immitance converter inserted between a receiving transducer and a pre-amplifier for amplifying the output of the receiving transducer. The damping admittance of the receiving transducer and the load admittance of the receiving transducer are offset by the negative admittance caused by the negative immitance converter.

3 Claims, 23 Drawing Figures

FIG.15 
— TIME

FIG.16 PRIOR ART 
— TIME

FIG.17 
— TIME

METHOD AND SYSTEM FOR TRANSMISSION AND RECEIPT OF MEASURING ULTRASONIC WAVE

CROSS-REFERENCE TO A RELATED APPLICATION

This invention is related to a U.S. Pat. application Ser. No. 881,678, filed on Feb. 16, 1978, now U.S. Pat. No. 4,156,823, in the name of Hideyuki Suzuki, one of the inventors of this invention.

BACKGROUND OF THE INVENTION

1. Field of the Invention

This invention relates to a method and a system for transmission and receipt of a measuring ultrasonic wave, or more in particular to a method and a system for measuring a gas concentration using the method of transmission and receipt of a measuring ultrasonic wave.

2. Description of the Prior Art

In driving an ultrasonic transducer (hereinafter referred to as the transducer) by electrical energy or using a transducer as an ultrasonic wave energy receiving element, delayed acoustic response characteristics caused by a high Q of the transducer or the presence of the damping impedance pose a problem. In order to improve the response characteristics, a method is used in which the transducer is mechanically damped or a damping resistor element suitable for the characteristics of the transducer is connected. In the mechanical damping method, it is impossible to attain a sufficient damping effect in the frequency range below 100 KHz, although comparatively satisfactory results are obtainable in the comparatively high frequency range of several hundred KHz. Also, both the methods have the disadvantage of a reduced receiving sensitivity of the receiver.

SUMMARY OF THE INVENTION

Accordingly, it is an object of the present invention to provide a method and a system for transmission and receipt of ultrasonic waves, which are superior in ultrasonic damping characteristics with high oscillation response and superior in both the reception oscillation response and sensitivity, without using the conventional method in which the transducer is mechanically damped or a damping resistor element suitable for the transducer characteristics is connected.

According to the present invention, there is provided a method and system for a measuring ultrasonic wave transmission and receipt, which are superior in response characterstics and sensitivity of transmission and recepit. Also, the method and system for measuring a gas concentration using the method and system for a measuring ultrasonic wave transmission and receipt according to the present invention are high in accuracy and applicable to a wide variety of object gases and very useful for industrial purposes.

DESCRIPTION OF THE PREFERRED EMBODIMENTS

The detailed description below of the method of ultrasonic wave transmission and receipt according to the present invention will be divided into ultrasonic wave transmission and ultrasonic wave receipt.

According to the method of damping for the ultrasonic wave transmission of the present invention, a negative immitance converter is inserted between a transducer and a drive amplifier for driving the transducer, so that the output impedance of the drive amplifier, the damping impedance of the transducer and the impedance between the transducer and the drive amplifier are offset by the negative impedance generated from the negative immitance converter. The method for damping according to the present invention will be described below in comparison with the conventional driving method.

Figure 1:
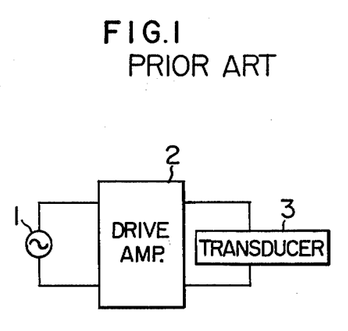
FIG. 1 is a block diagram showing a conventional ultrasonic wave transmitter.

A block diagram for explaining the conventional method for driving a transducer is shown in FIG. 1. In the drawing under consideration, reference numeral 1 shows a signal oscillator, numeral 2 a drive amplifier, and numeral 3 a transducer.

Figure 2:
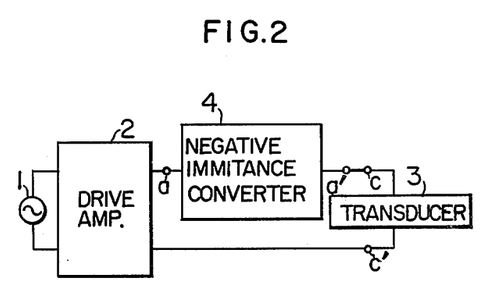
FIG. 2 is a block diagram showing an ultrasonic wave transmitter according to the present invention.

A block diagram for explaining a method for damping the transducer according to the present invention is shown in FIG. 2. In the drawing under consideration, numeral 1 shows a signal oscillator, numeral 2 is a drive amplifier, numeral 3 a transducer element and numeral 4 a negative immitance converter.

Figure 3:
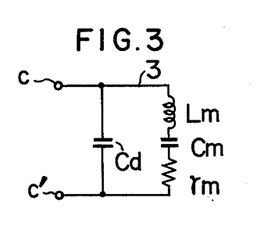
FIG. 3 shows an equivalent circuit of an electrostrictive element.

An equivalent circuit of an electrostrictive element is shown in FIG. 3. In the drawing, Cd shows a damping capacitance, Lm an equivalent inductance, Cm an equivalent capacitance, and $r_m$ an equivalent resistance. Let the equivalent mass of the transducer be M, the equivalent stiffness thereof be S, the equivalent mechanical resistance of the transducer including the acoustic radiation resistance be $R_M$, and the force factor of the transducer be A. Lm, Cm and $r_m$ are given by the equations below respectively.

$$Lm = M/A^2, \ Cm = A^2S, \ r_m = R_M/A^2$$

Figure 4:
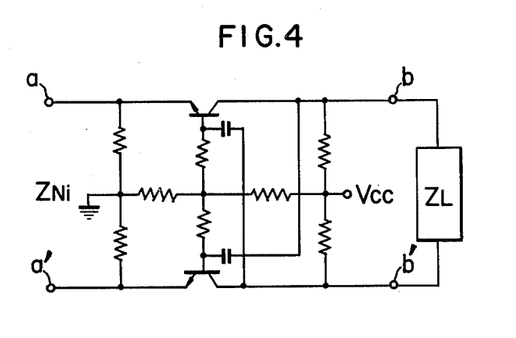
FIG. 4 is a circuit diagram showing a circuit example of a negative immitance converter.

A circuit diagram of an example of the configuration of the negative immitance converter is shown in FIG. 4. Let the input impedance as viewed from the terminals a-a' be $Z_{Ni}$, and the impedance as viewed from the terminals b-b' be $Z_L$. The relation below is obtained.

$$Z_{Ni} = -kZ_L \tag{1}$$

where K is a positive constant determined by the circuit constant of the negative immitance converter. The negative immitance converter is generally divided, in terms of circuit configuration, into an open-stable negative immitance converter and a short-circuited stable negative immitance converter. The converter shown in FIG. 4 belongs to the former category.

Figure 5:
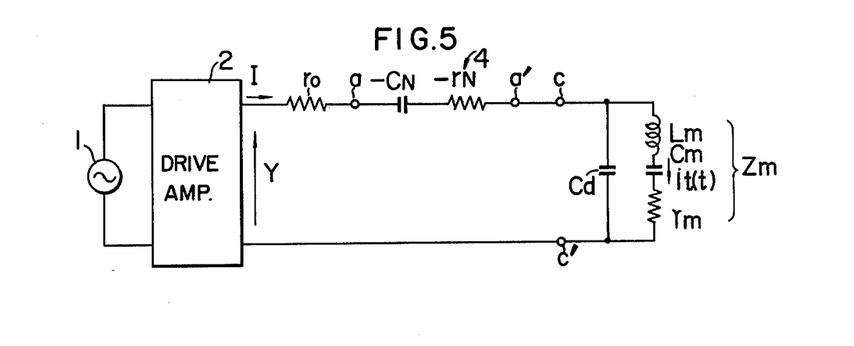
FIG. 5 is a diagram showing a model operation of the transmitter according to the present invention.

Next, the damping effect achieved by the method according to the present invention will be explained. A model of ultrasonic wave drive according to the present invention is shown in FIG. 5. In this model, the following basic equation concerning the electro-mechanical conversion is established:

$$\left. \begin{array}{l} F = -AV + A^2/Ym \cdot \dot{V} \\ I = (Yo' + Yd)V + A\dot{V} \end{array} \right\} \tag{2}$$

In the model of FIG. 5, numeral 1 shows a signal oscillator, numeral 2 a drive amplifier, character Y an output voltage of the amplifier, character I an output electric current of the amplifier 2, and $r_O$ an output impedance of the amplifier 2. $-C_N$ and $-r_N$ are negative immitance components generated from the negative immitance converter as shown in equation (1). Characters it(t) show the electric current flowing in the dynamic impedance of the transducer. In equation (2), character F shows an external force exerted on the transmitter, $Ym = 1/Zm$ the dynamic admittance of the transducer, and character $\dot{V}$ the vibrating speed of the transducer. Yo' is the admittance as viewed toward the left from the terminals C-C' in FIG. 5, and Yd the admittance of the transducer.

From equation (2), the value V for zero of F is determined. As a result, the equation (3) below is obtained.

$$\dot{V}(t) = (1/A) \cdot Ym/(Ym + Yd + Yo') \cdot I = (1/A) \cdot it(t) \tag{3}$$

In order to determine the response of it(t), It(s) which is a Laplace's transformation of it(t) is determined from FIG. 5. The equation (4) below is obtained.

$$It(s) = [V(s)/CdS]1/[(r_O - r_N + 1/CdS - 1/C_NS) \cdot (r_m + LmS + 1/CdS + 1/CmS) - 1/Cd^2S^2] \tag{4}$$

On the assumption that the negative impedance $Z_{Ni}$ of the negative immitance converter shown in FIG. 2 is expressed by the equation (5) below, the value $Z_L$ in FIG. 4 is determined in such a manner that equations (6) and (7) below are established in equation (4). In other words, by equalizing the combined impedance of the damping impedance of the transducer and the output impedance of the drive amplifier to the input negative immitance of the negative immitance converter, equation (4) is rewritten to equation (8) as follows:

$$Z_{Ni} = -1/C_NS - r_N \tag{5}$$

$$Cd = C_N \tag{6}$$

$$r_O = r_N \tag{7}$$

$$It(s) = -V(s)CdS \tag{8}$$

Figure 6:
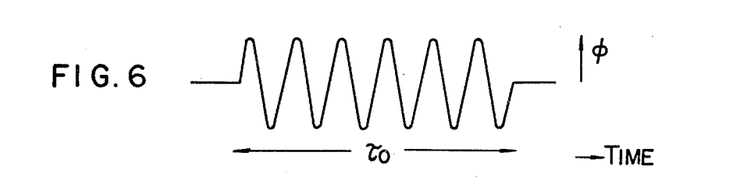
FIG. 6 is a diagram showing an output waveform of the drive amplifier.
Figure 7:
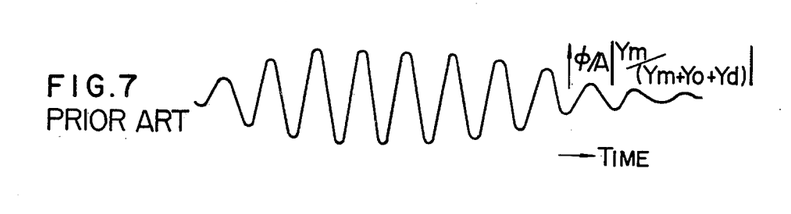
FIG. 7 is a diagram showing a transducer velocity waveform for a conventional method.

A pulse-width modulated sine-wave output V of the drive amplifier is shown in FIG. 6. The diagram of FIG. 7 shows a waveform of vibrating speed obtained when the transducer 3 of the transmitter according to the conventional method of FIG. 1 is driven by the output V. The signal V of FIG. 6 and the Laplace's transformation V(s) thereof are given by equations (9) and (10) respectively.

$$V = \phi \cdot [\sin \omega t - \sin \omega(t - \tau_o) \cdot h(t - \tau_o)] \tag{9}$$

$$V(s) = \phi \cdot [\omega/(S^2 + \omega^2)] \cdot (1 - e^{-\tau_o S}) \tag{10}$$

where $\phi$ is the amplitude of the drive signal, $\omega$ an angular frequency, $\tau_o$ pulse width, and $h(t - \tau_o)$ a time shaft function. From equations (10) and (8), It(S) is given as equation (11) below, and the vibrating speed of the transducer $\dot{V}(S)$ as equation (12). Returning the coordinate axis to time axis by Laplace's inverse transformation of equation (12), equation (13) is obtained.

$$It(s) = -\omega Cd \cdot \phi [S/(s^2 + \omega^2)] \cdot (1 - e^{-\tau_o S}) \tag{11}$$

$$\dot{V}(s) = -\omega Cd(\phi/A) \cdot [S/(s^2 + \omega^2)] \cdot (1 - e^{-\tau_o S}) \tag{12}$$

$$\dot{V}(t) = -\omega Cd(\omega/A) \cdot [\cos \omega t - (\cos \omega)(t - \tau_o)h(t - \tau_o)] \tag{13}$$

Figure 8:
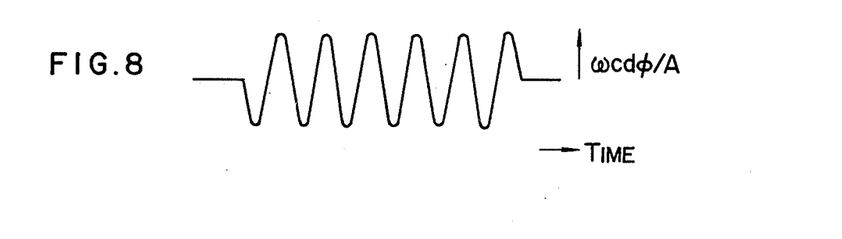
FIG. 8 is a diagram showing a transducer velocity waveform according to the present invention.

The diagram of FIG. 8 shows a waveform of the vibrating speed for equation (13), i.e., based on the method of the present invention. It is seen from FIG. 8 that complete damping effect is achieved.

Figure 9:
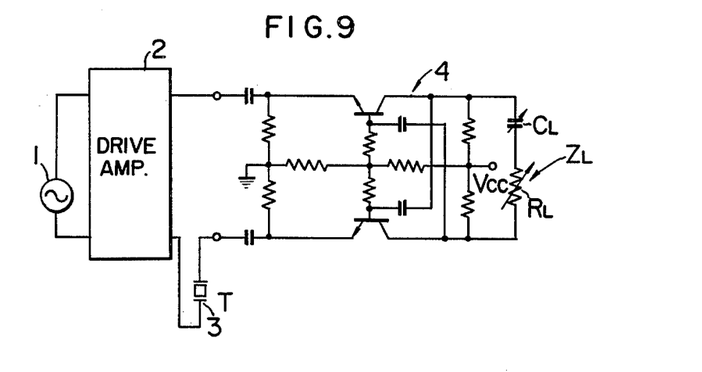
FIG. 9 is a circuit diagram showing an embodiment of the transmitter according to the present invention.

A circuit diagram of an embodiment of the transmitter using the method according to the invention is shown in FIG. 9. In the drawing, numeral 1 shows a signal oscillator, numeral 2 a drive amplifier, numeral 3 a transducer, and $Z_L$ a load of the negative immitance converter.

Next, a method for receiving an ultrasonic wave according to the present invention will be described in detail. According to the method for receiving ultrasonic energy according to the present invention, a negative immitance converter is inserted between a transducer and a pre-amplifier for amplifying the output of the transducer, so that the damping admittance of the transducer and the load admittance of the transducer are offset by the negative admittance generated by the negative immitance converter.

By configuring the ultrasonic wave receiver according to the above-mentioned method, the response damping characteristics and sensitivity are maintained at high level, thus making it possible to achieve the object of the invention.

Figures 10, 11:
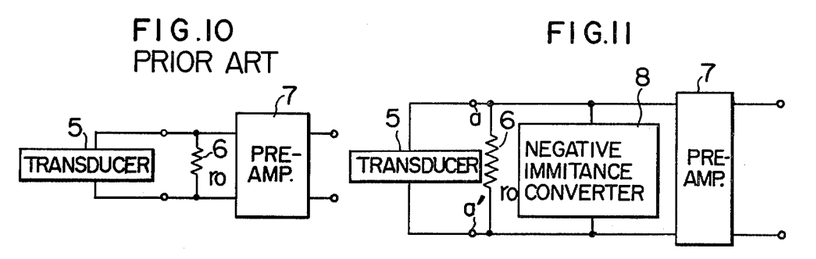
FIG. 10 is a block diagram showing a conventional ultrasonic wave receiver.
FIG. 11 is a block diagram shwoing an ultrasonic wave receiver according to the present invention.
Figure 12:
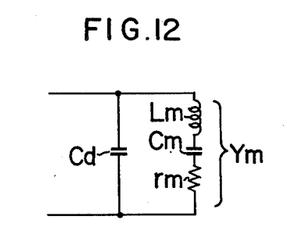
FIG. 12 is a diagram showing an equivalent circuit of the electrostrictive element.

The method according to the invention will be described in detail below in comparison with a conventional method. FIG. 10 is a block diagram showing a receiver constructed by the conventional method. In the drawing under consideration, numeral 5 shows a transducer, numeral 6 a damping resistor, and numeral 7 a pre-amplifier. A block diagram of the receiver constructed according the method of the invention is shown in FIG. 11. Numeral 5 shows a transducer, numeral 6 a resistor, numeral 7 a pre-amplifier, and numeral 8 a negative immitance converter. The diagram of FIG. 12 shows an equivalent circuit of the transducer. In the drawing under consideration, Cd shows a damping capacitance, Lm an equivalent inductance of the transducer, Cm an equivalent resistance of the transducer, and $r_m$ an equivalent resistance of the transducer. Let the equivalent mass of transducer be M, the equivalent stiffness of the transducer be S, the equivalent mechanical resistance of the transducer be $R_M$, and the force factor of the transducer be A. And Lm, Cm and $r_m$ are given by the equations below respectively.

$$Lm = M/A^2, \; Cm = A^2/S, \; r_m = R_M/A^2$$

Figure 13:
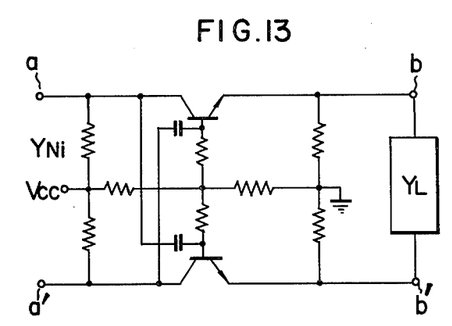
FIG. 13 is a circuit diagram showing an example of the negative immitance converter.

A circuit diagram showing an example of the negative immitance converter is illustrated in FIG. 13. The relation between the input admittance $Y_{Ni}$ of the negative immitance converter as viewed from the terminals a–a' and the admittance $Y_L$ connected between the terminals b and b' is given by the equation below.

$$Y_{Ni} = -KY_L \quad (14)$$

where K is a positive constant determined by the circuit constant of the converter. Depending on the circuit configuration, the negative immitance converter is generally divided into an open-stable type negative immitance converter and a short-circuited stable type negative immitance converter. The converter shown in the drawing belongs to the latter category.

Figure 14:
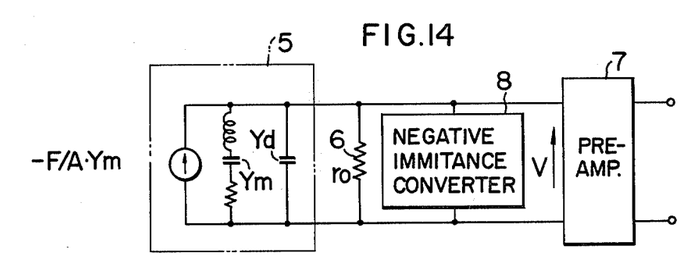
FIG. 14 shows a model of the receiving operation of the receiver according to the present invention.

The damping effect at the time of reception by the receiver constructed by the method according to the present invention will be described below. The diagram of FIG. 14 shows a model of the receiving operation of the receiver. In this model, the basic formula for electro-mechanical conversion is expressed as $$\left. \begin{array}{l} F = -AV + A^2/Ym \cdot \dot{V} \\ I = (Yo + Yd)V + A \cdot \dot{V} \end{array} \right\} \quad (15)$$

From this, the output V of the receiver is given by equation (16) by substituting I=0 into equation (15).

$$V = -(F/A) \cdot Ym/(Ym + Yo + Yd) \quad (16)$$

where F is a mechanical input, Ym the admittance of the transducer given as 1/Zm, and Yo the admittance as viewed rightward from the terminals a–a $\propto$ in FIG. 11. In FIG. 14, the section surrounded by the two-dot chain is an equivalent circuit of the transducer at the time of reception, numeral 8 a negative immitance converter, numeral 7 a pre-amplifier, and V the output voltage of the receiver. In order to consider the response of the output voltage at the time of receipt, Laplace's transformation is effected on the basis of FIG. 14, and equation (17) below is obtained.

$$V(s) = -[F(s)/A] \cdot Ym(s)/[Ym(s) + Yo(s) + Yd(s)] \quad (17)$$

If the admittance Yo in FIG. 14 is Yo'(s), Yo is given by equation (18) below in the form of Yo'(s) and the admittance $Y_{Ni}(s)$ of the negative immitance converter 8. Thus equation (17) is rewritten as equation (19).

$$Yo(s) = Yo'(s) + Y_{Ni}(s) \quad (18)$$

$$V(s) = -(F(s)/A) \cdot Ym(s)/[Ym(s) + Yo'(s) + Y_{Ni}(s) + Yd(s)] \quad (19)$$

If equation (20) is satisfied, equation (19) is rewritten as equation (21) below.

$$Yo'(s) + Y_{Ni}(s) + Yd(s) = 0 \quad (20)$$

$$V(s) = -F(s)/A \quad (21)$$

Equation (22) below shows the ratio between the wave-receiving sensitivity for the method according to the present invention and that for the conventional method.

$$G = 1 + |(Yo + Yd)/Ym| \quad (22)$$

It is seen that the output voltage, i.e., the response of the output of the ultrasonic wave receiver to the mechanical input signal is improved to a great extent, thus improving the wave-receiving sensitivity.

The conditions satisfying equation (20) will be described below. Assuming that $Y_L$ shown in equation (14) is a parallel admittance of $R_L$ and $C_L$, the condition of equation (20) is established when the relations of equations (23) and (24) below exist.

$$Vo = R_L/K \quad (23)$$

$$Cd = KC_L \quad (24)$$

When this condition is satisfied, V(t) is given by the following equation (25) by Laplace's inverse transformation of equation (21).

$$V(t) = -F(t)/A \quad (25)$$

Figure 15:
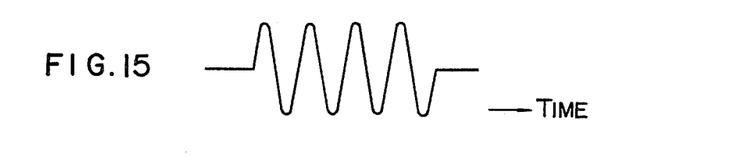
FIG. 15 is a graph showing a receiver input signal.
Figure 16:
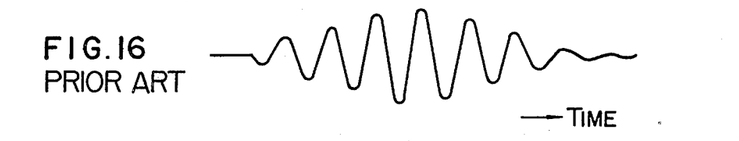
FIG. 16 is a graph showing an output signal of the receiver for the conventional method.
Figure 17:
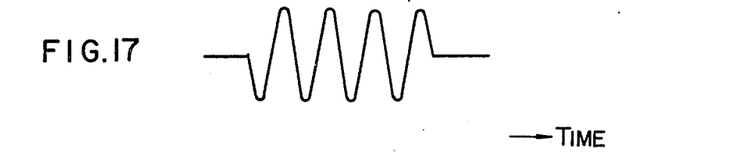
FIG. 17 is a graph showing an output signal of the receiver according to the present invention.

The diagram of FIG. 15 shows a waveform of the input signal F(t) of the receiver, and that of FIG. 16 a waveform of the output of the receiver according to the conventional method. FIG. 17 shows a waveform of the output produced by the system constructed by the method according to the present invention. As apparent from these drawings, the transient response characteristics are thoroughly improved by the present invention.

Figure 18:
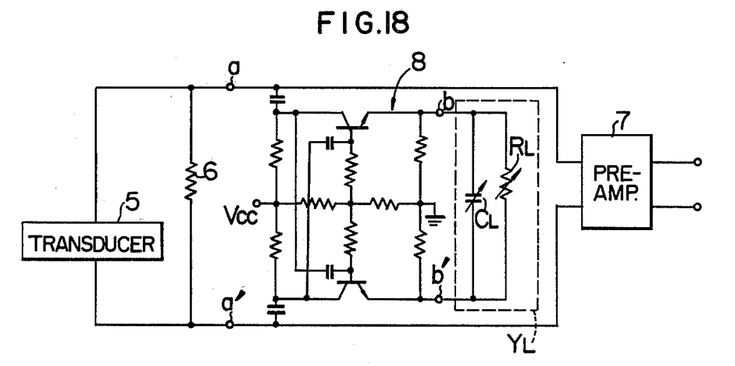
FIG. 18 is a circuit diagram showing an example of the configuration of the receiver according to the present invention.

An embodiment of the receiver constructed by the method according to the present invention is shown in FIG. 18. In this drawing, numeral 5 shows a transducer, numeral 6 a resistor, numeral 7 a pre-amplifier and numeral 8 a negative immitance converter. $Y_L$ shows a load admittance of the negative immitance converter 8 comprised of a parallel circuit of $R_L$ and $C_L$.

As is obvious from the foregoing explanation, the method for ultrasonic wave transmission and receipt according to the present invention is such that the negative immitance converter produces a negative impedance offsetting the output impedance of the drive amplifier of the ultrasonic transmitter and the damping impedance of the transducer, thus making possible ideal damping over a wide range of ultrasonic frequencies. Further, the admittance of the transducer of the ultrasonic wave receiver and the admittance externally connected to the transducer are thoroughly offset by the negative admittance generated by the negative immitance converter. This method of ultrasonic wave transmission and receipt provides superior response characteristics and transmission and receipt sensitivity.

A method and system for measuring a gas concentration to which the method and system for a measuring ultrasonic wave transmission and receipt according to the present invention is applicable will be explained in detail below.

The propagation speed of ultrasonic wave in a mixture gas is determined only by the constants, concentration and temperature of the mixture gas and expressed by equation (26) below.

$$v^2 = \sum_i C_{pi} X_i / \sum_i C_{vi} X_i \cdot 1 / \sum_i M_i X_i \cdot R \cdot T \tag{26}$$

where v is the propagation speed of ultrasonic wave propagation in the mixture gas, Cpi specific heat at constant pressure of the object gas i in the mixture gas, Cvi the specific heat at constant volume of the object gas i in the mixture gas, Mi the molecular weight of the object gas i in the mixture gas, Xi the molar fraction of the object gas i in the mixture gas, R a gas constant, and T the absolute temperature of the mixture gas.

Assuming that the mixture gas is comprised of air and $CO_2$, equation (26) is rewritten as $$v^2 = (C_{pCO_2} X_{CO_2} + C_{pair} X_{air})/(C_{vCO_2} X_{CO_2} + C_{vair} X_{air}) \cdot R \cdot T \tag{27}$$

Figure 19:
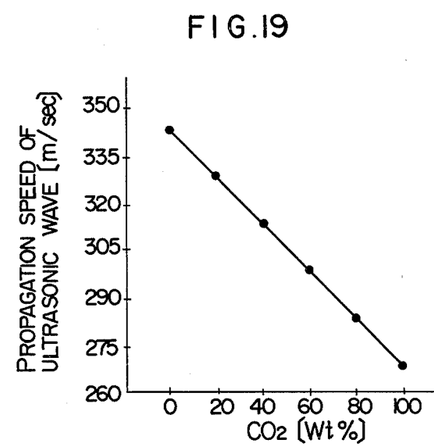
FIG. 19 is a graph showing the relation between $CO_2$ gas concentration and propagation speed of ultrasonic wave.

With the constants replaced by the corresponding figures, the propagation speed of ultrasonic wave at each concentration of $CO_2$ at the absolute temperature 293° K. of the mixture gas is calculated and shown by graph in FIG. 19. Since $\Sigma X_i = 1$, equation (27) is alternatively given as equation (28) below.

$$v^2 = \frac{[C_{pair} + (C_{pCO_2} - C_{pair}) X_{CO_2}]}{[C_{vair} + (C_{vCO_2} - C_{vair}) X_{CO_2}]} \times \frac{R \cdot T}{[M_{air} + (M_{CO_2} - M_{air}) X_{CO_2}]} = G(X_2, T) \tag{28}$$

From equation (28), the concentration $X_{CO_2}$ is given as equation (29) below.

$$X_{CO_2} = F(v, T) \tag{29}$$

Thus, the concentration of the object gas is a function of the propagation speed of ultrasonic wave v and the gas temperature T.

Figure 20:
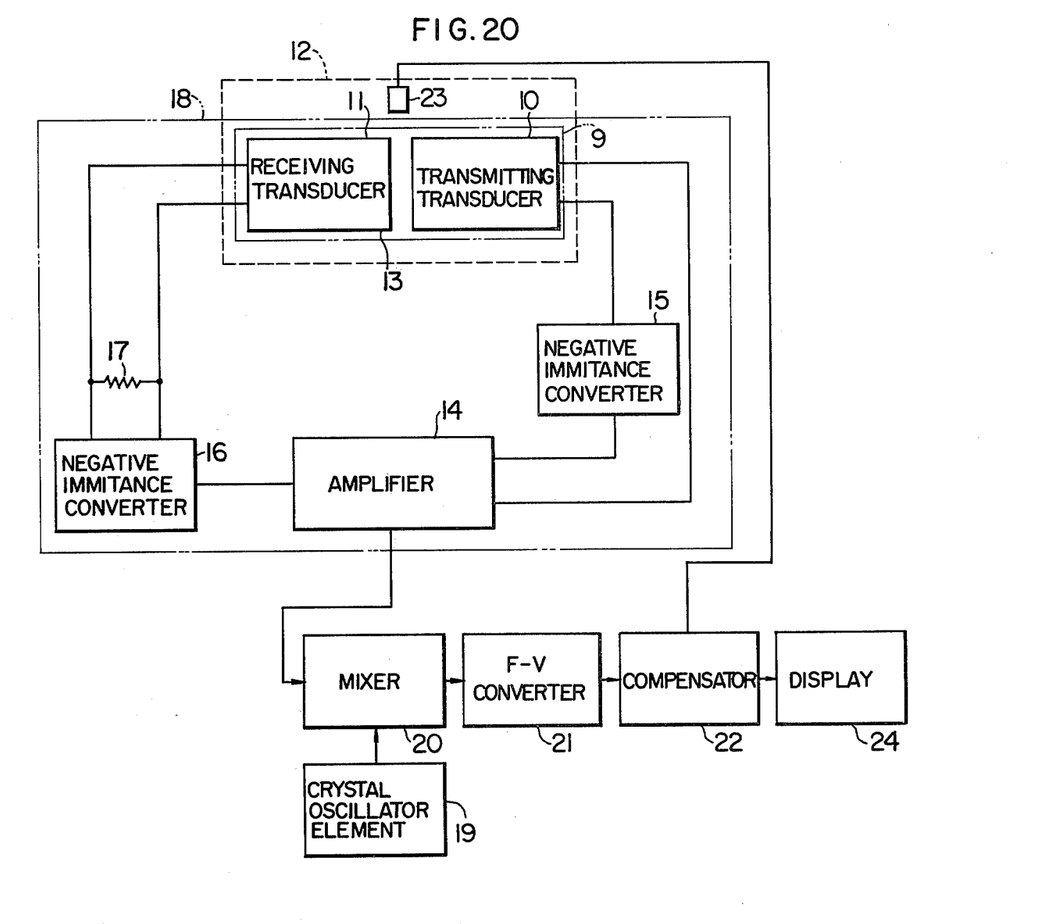
FIG. 20 is a block diagram showing an embodiment of a gas concentration measuring system according to the present invention.

An embodiment of the gas concentration measuring system according to the present invention, designed on the basis of the above-mentioned theory, will be explained below with reference to FIG. 20.

An ultrasonic sensor 9 includes a transmitting transducer 10 and a receiving transducer 11 disposed opposedly to the transmitting transducer 10. The ultrasonic sensor 9 is mounted within an object gas atmosphere 12 by a proper method. The ultrasonic wave transmitted from the transmitting transducer 10 is passed through the ultrasonic wave path 13 containing the object gas and received by the receiving transducer 11. The speed at which the ultrasonic wave passes through the ultrasonic wave path 13 is inversely proportional to the concentration of the object gas. The transmitting transducer 10 comprises an electrostrictive element.

The amplifier 14 includes the functions of the signal oscillator 1 and the drive amplifier 2. By inserting the negative immitance converter 15 between the transmitting transducer 10 and the amplifier 14, impedances including damping impedance of the transmitting transducer 10, output impedance of the amplifier 14 and impedance between the transmitting transducer 10 and the amplifier 14 are offset by negative impedance generated by the negative immitance converter 15.

The amplifier 14 also includes the function of the pre-amplifier 7. The receiving transducer 11 comprises an electrostrictive element. By inserting another negative immitance converter 16 and the resistor 17 between the receiving transducer 11 at a receiving end for receiving the ultrasonic wave and converting it into electric energy and the amplifier 14 for amplifying an output of the receiving transducer 11, admittances including load admittance and damping impedance of the receiving transducer 11 at the receiving end are offset by the negative admittance generated by the negative admittance generated by the negative immitance converter 16.

On the other hand, the frequency fm of the feedback oscillator system 18 is so related to the propagation speed v of the ultrasonic wave in the object mixture gas that $fm = k \cdot v / l$, where l is distance between the transmitting transducer 10 and the receiving transducer 11, and k a constant of proportionality. Thus, the frequency fm of the feedback oscillating system 18 and the stable reference frequency fo generated from the crystal oscillator element 19 are applied to the mixer 20, where the difference F between fm and fo is determined. This value F is converted into a voltage by the frequency-voltage converter 21 and applied to the compensator 22.

A temperaure sensor 23 comprises a thermistor, a temperature measuring resistor or a kind of thermocouple for measuring the temperature of the object gas atmosphere 12. The resulting temperature data is applied to the compensator 22 for temperature compensation by which the temperature dependency of the propagation speed of ultrasonic wave is eliminated. The temperature-compensated output voltage is indicated on the display unit 24 comprising an analog voltmeter, digital voltmeter or recorder.

Figure 21:
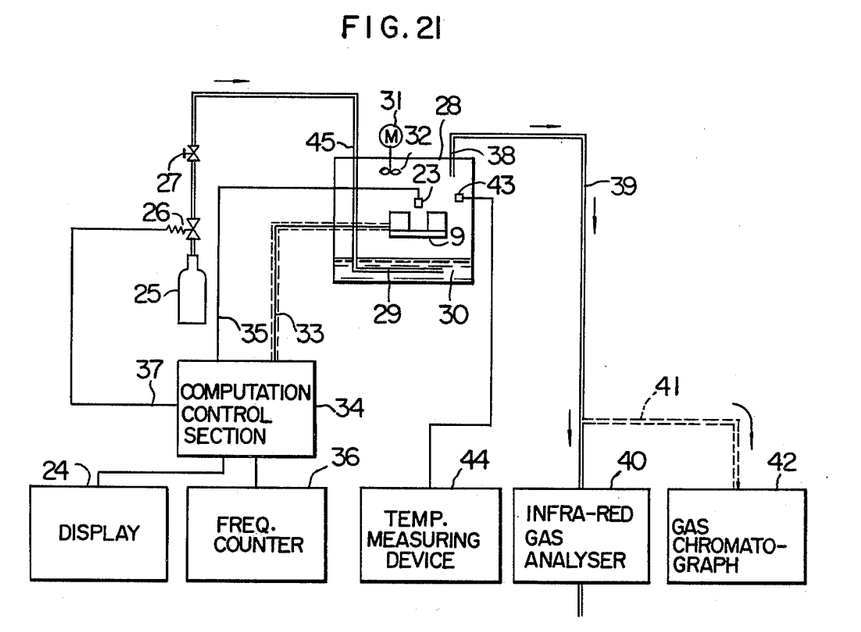
FIG. 21 is a schematic diagram showing an embodiment of a system for measuring and controlling the gas concentration according to the present invention.

Now, an embodiment of the method and system for measuring and controlling, by the ultrasonic wave gas concentration measuring system according to the present invention, the concentration of $CO_2$ gas in a mixture gas comprising air, $CO_2$ and $H_2O$ of a tissue culture device according to the invention, will be described in detail with reference to FIGS. 20 and 21.

The $CO_2$ gas in the gas cylinder 25 containing 100% $CO_2$ gas is introduced to the tissue culture device 28 (hereinafter referred to as the culture device) from the lead tube 29 in the culture device 28 through the solenoid valve 26 and the flow-rate regulation valve 27. A water bath 30 sufficiently deep to immerse the lead tube 29 is provided on the bottom of the culture device 28. From a gas blow-off hole provided appropriately in the lead tube 29, the $CO_2$ gas is blown off into the culture device 28 through the water bath 30. By doing so, the relative humidity in the culture device 28 increases to as high as 95 to 100%. Blade-type agitator 32 driven by a motor 31 is provided above the culture device 28 and operated to make uniform the concentration of the $CO_2$ gas in the culture device 28. The ultrasonic sensor 9 according to the present invention is disposed at an appropriate position in the culture device 28, and connected by a shielded cable 33 to a computation control section 34 including the feedback oscillating system 18, the crystal oscillator element 19, the mixer 20, the frequency-voltage converter 21 and the compensator 22. The temperature-compensating temperature sensor 23 including a temperature-measuring resistor is connected to the compensator 22 of the computation control section 34 by the cable 35. The output voltage from the compensator 22 is set at 0 to 20 V against the $CO_2$ gas concentration of 0 to 20% by volume, so that the reading of output voltage represents the $CO_2$ gas concentration. As the display unit 24, a digital voltmeter is used, and the frequency fm of the feedback oscillating system 18 is monitored by the frequency counter 36. The computation control section 34 has a source of reference voltage with a predetermined range, which is adapted to be variably set within a range from 0 to 20 V. In the case where the lower limit of the reference voltage value is exceeded, the solenoid valve 26 is released, so that $CO_2$ gas flows into the culture device 28. When the upper limit of the reference voltage value is exceeded, on the other hand, the solenoid valve 26 is closed, so that the $CO_2$ gas stops flowing into the culture device 28. This flow control is effected by a control mechanism incorporated in the computation control section 34. A signal from the control mechanism is transmitted by cable 37 to the solenoid valve 26. The culture device 28 has a sampling hole 38 for sampling the mixture gas in the culture device 28, so that the sample collected is introduced through the sampling pipe 39 to the infrared ray gas analyzer 40 capable of continuous measurement of $CO_2$ gas concentration. A sampling port 41 for a gas chromatograph is provided midway of the sampling pipe 39, so that the $CO_2$ gas concentration is checked by the gas chromatograph 42.

The culture device 28 contains a thermistor temperature sensor 43 for measuring the temperature of the gas in the culture device 28, which temperature sensor 43 is monitored by the temperature measuring device 44. The culture device 28 is a completely hermetic system except for the $CO_2$ gas inlet pipe 45 and the sampling hole 38. The culture device 28 is temperature-controlled at ±0.1° C. by a water jacket system, and the gas temperature in the culture device 28 is variable within the range from 0° to 50° C.

By using the above-mentioned system, the temperature within the culture device 28 is changed to 27° C., 35° C. and 42° C., and at each temperature, the $CO_2$ gas concentration is changed from 0 to 20%. The result of examination by the infrared ray gas analyzer 40 and the gas chromatograph 42 is shown in Table 1 and FIG. 22.

Figure 22:
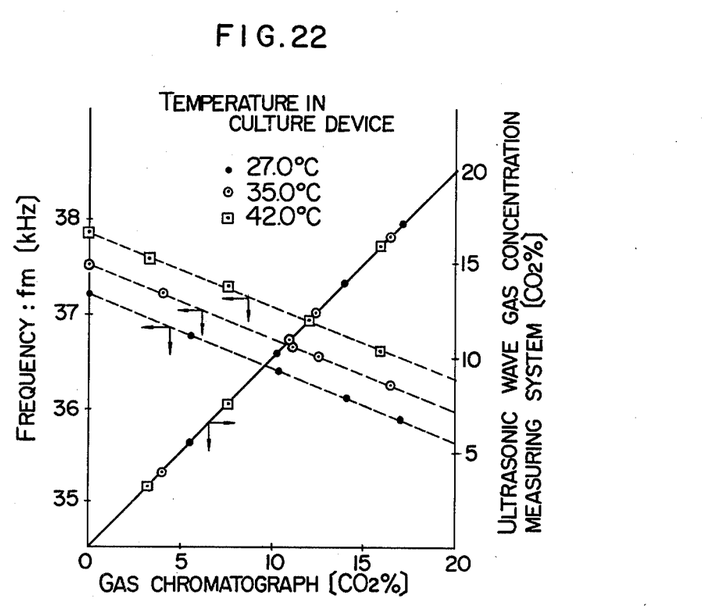
FIG. 22 is a graph drawn from Table 1.

From Table 1 and FIG. 22, it is seen that the frequency fm of the feedback oscillating system of the ultrasonic wave gas concentration measuring system according to the present invention represents a linear characteristic against the concentration indicated by the gas chromatograph and the infrared ray gas analyzer, and that the concentration indicated by the ultrasonic wave gas concentration measuring system is sufficiently identical to the concentration indicated by the gas chromatograph and the infrared ray gas analyzer.

Although the foregoing description concerns an embodiment of the method and system for measuring the gas concentration according to the present invention including the three gas components of $CO_2$, air and $H_2O$, the present invention is not of course limited to such a composition of the gas. It is noted that the method and system of the present invention includes the case where a receiving transducer is arranged to receive an echo beam caused by the ultrasonic wave which is transmitted to the object from a transmitting transducer. Further, it is also noted that the receiving transmitter may receive the ultrasonic wave through a reflector.

Figure 23:
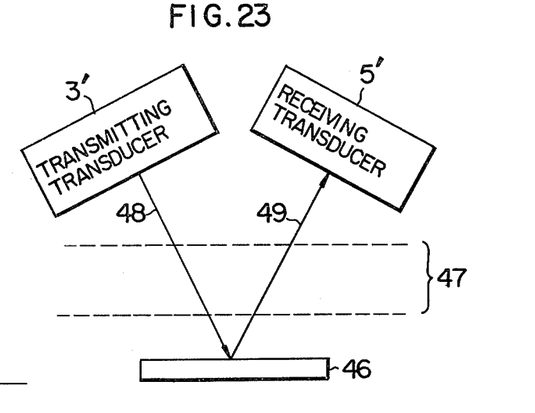
FIG. 23 is a schematic diagram shwoing another embodiment of the present invention.

FIG. 23 is a schematic diagram showing another embodiment of the principal part of the present invention. In the figure, a transmitting transducer 3' and a receiving transducer 5' are arranged so that the receiving transducer 5' receives an ultrasonic wave echo 49 reflected by a reflex plate 46 or the like which has a function to reflect an ultrasonic wave 48 transmitted from a transmitter transducer 3' through an object 47 to be measured.

Table 1

| Temp. in culture device [°C.] | Reading on ultrasonic wave gas concentration measuring system [Vol %] | Frequency of ultrasonic wave gas concentration measuring system fm[KHz] | Concentration on gas chromatograph [Vol %] | Concentration on infrared ray gas analyzer [Vol %] |
| --- | --- | --- | --- | --- |
|  | 0 | 37.200 | 0 | 0 |
|  | 5.6 | 36.752 | 5.58 | 5.6 |
| 27.0 | 10.4 | 36.370 | 10.36 | 10.5 |
|  | 14.1 | 36.075 | 14.14 | 14.1 |
|  | 17.1 | 35.835 | 17.16 | 17.2 |
|  | 0 | 37.536 | 0 | 0 |
|  | 4.1 | 37.205 | 4.07 | 4.2 |
| 35.0 | 11.0 | 36.652 | 11.04 | 11.2 |
|  | 12.5 | 36.535 | 12.48 | 12.8 |
|  | 16.6 | 36.209 | 16.63 | 16.9 |
|  | 0 | 37.870 | 0 | 0 |
|  | 3.4 | 37.596 | 3.37 | 3.4 |
| 42.0 | 7.6 | 37.265 | 7.62 | 7.9 |
|  | 12.2 | 36.890 | 12.19 | 12.6 |
|  | 15.8 | 36.606 | 15.84 | 16.4 |

We claim:

1. A method for measuring a gas concentration comprising the steps of:

(a) transmitting an ultrasonic wave from a transmitting transducer through an object gas atmosphere to a receiving transducer, said transmitting transducer including an electrostrictive element controlled by a circuit by which negative impedance generated from a negative immitance converter offsets impedances including damping impedance of said transmitting transducer, output impedance of an amplifier for driving said transmitting transducer and impedance between said transmitting transducer and said amplifier, said negative immitance converter being inserted between said transmitting transducer and said amplifier, and said receiving transducer for receiving the ultrasonic wave and converting it into electric energy including an electrostrictive element controlled by a circuit by which negative admittance generated by another negative immitance converter inserted between said receiving transducer and said amplifier which also amplifies an output of said receiving transducer offsets admittances including load admittance and damping impedance of said receiving transducer; and (b) converting the difference between the frequency of a feedback oscillating system constituted by both said negative immitance converters and said amplifier which also functions feedback oscillation and a stable reference frequency into a voltage indicative of the concentration of an object gas in said object gas atmosphere.

2. A gas concentration measuring system comprising:

a circuit including an amplifier, a transmitting transducer having an electrostrictive element for converting an ultrasonic wave signal amplified by said amplifier, and a negative immitance converter inserted between said amplifier and said transmitting transducer;

a circuit including an receiving transducer having another electrostrictive element for receiving an ultrasonic wave and converting it into electric energy, said another electrostrictive element being disposed oppositely to said transmitting transducer so as to receive the ultrasonic wave from said transmitting transducer through an object gas atmosphere, a resistor connected in parallel to said receiving transducer and another negative immitance converter which are applied to said amplifier, both said circuits making up a feedback oscillating system; and a mixer for calculating difference between the frequency of said feedback oscillating system and a stable reference frequency, and a frequency-voltage converter responsive to a frequency input thereto calculated by said mixer, for producing a voltage indicative of the concentration of an object gas in said object gas atmosphere.

3. A tissue culture device using the measuring system according to claim 2, comprising:

a tissue culture chamber containing therein the object gas atmosphere of $CO_2$ gas which is the object gas to be measured, air and water vapor; and a $CO_2$ gas concentration control mechanism for effecting a selected amount of $CO_2$ gas supply into said chamber when the $CO_2$ gas concentration measured by said measuring system deviates out of a predetermined reference range.

* * * * *